United States Patent
Lee et al.

(10) Patent No.: US 7,762,952 B2
(45) Date of Patent: Jul. 27, 2010

(54) METHOD, MEDIUM, AND APPARATUS FOR PORTABLY MEASURING CALORIE CONSUMPTION

(75) Inventors: Mi-Hee Lee, Yongin-si (KR); Seokwon Bang, Seoul (KR); Hyounggi Lee, Suwon-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 1430 days.

(21) Appl. No.: 11/095,551

(22) Filed: Apr. 1, 2005

(65) Prior Publication Data

US 2006/0084851 A1 Apr. 20, 2006

(30) Foreign Application Priority Data

Oct. 14, 2004 (KR) .................... 10-2004-0082074

(51) Int. Cl.
*A61B 5/00* (2006.01)
(52) U.S. Cl. .................................................... 600/300
(58) Field of Classification Search ................ 600/543, 600/300, 301; 482/8
See application file for complete search history.

(56) References Cited

U.S. PATENT DOCUMENTS

| 5,918,603 | A | 7/1999 | Brown | 128/897 |
| 2002/0019585 | A1* | 2/2002 | Dickinson | 600/300 |
| 2004/0117212 | A1 | 6/2004 | Kong et al. | |

FOREIGN PATENT DOCUMENTS

| JP | 02-080029 | 3/1990 |
| JP | 08-052119 | 2/1996 |
| JP | 2004-130142 | 4/2004 |
| WO | 2004/109755 | 12/2004 |

OTHER PUBLICATIONS

Patrick Houston, "Samsung Yepp Sport YP-60V: At a glance", Aug. 5, 2004, CNET, p. 2-3.*
European Search Report dated Feb. 7, 2006 for European Application No. 05256394.7.
Samsung's Digital World—Press Release, "Samsung Outruns The Competition With The YP-60 Sports Yepp", Oct. 29, 2004, pp. 35.

* cited by examiner

*Primary Examiner*—Charles A Marmor, II
*Assistant Examiner*—Christian Jang
(74) *Attorney, Agent, or Firm*—Staas & Halsey LLP (57) ABSTRACT

A measuring device for use in measuring calorie consumption includes a pulse input unit which detects a first heart rate of the user at a first point in an exercise period and a second heart rate of the user at a second point of the exercise period other than the first point, the pulse input unit not detecting a third heart rate between the first and second heart rates; and a controller which receives the detected first and second heart rates and calculates calories consumed using the detected first heart rate, the detected second heart rate, an at rest heart rate of the user, and one or more of an age of the user, gender of the user, weight of the user, height of the user, and an at rest heart rate of the user. The measuring device is usable in a portable device, such as a portable digital audio and/or video reproducing apparatus.

18 Claims, 5 Drawing Sheets

METHOD, MEDIUM, AND APPARATUS FOR PORTABLY MEASURING CALORIE CONSUMPTION

BACKGROUND OF THE INVENTION

1. Field of the Invention

The invention relates to a method and apparatus for measuring heart rate, and more particularly, to a method and apparatus that can calculate calorie usage using the heart rate measured at discrete times.

2. Description of the Related Art

In general, there are two basic techniques for measuring calorie usage. The first method is a direct method in which the heat given off by the body is directly measured. The second method is an indirect method in which the heart rate is used to estimate the calorie usage as discussed in Japanese Patent Publication No. 02-080029. However, when measuring calorie consumption using the indirect method, there generally is a need for separate machinery and/or apparatus, which makes the measurement impractical when the calorie consumption is being measured by a portable device or a general device not dedicated to measuring calorie consumption. In addition, the indirect method discussed in Japanese Patent Publication No. 02-080029 generally requires continuous measurement of the heart rate during exercise, which is often not practical or desirable for general or portable devices having more limited memory.

SUMMARY OF THE INVENTION

An aspect of the invention provides a method of measuring calorie usage that only uses the heart rates at predetermined times, such as before and after exercise, and does not require continuous monitoring of the heart rates over the exercise period and/or for sustained portions of the exercise period.

According to an aspect of the invention, the method is implemented as software using a portable digital audio player having a pulse input unit and which is effective to calculate the calories consumed using discrete measurements of the heart rates before and after exercise.

According to an aspect of the invention, a measuring device for use in measuring calories consumed by a user includes a pulse input unit which detects a first heart rate of the user at a first point in an exercise period and a second heart rate of the user at a second point of the exercise period other than the first point, the pulse input unit not detecting a third heart rate between the first and second points; and a controller which receives the detected first and second heart rates and calculates calories consumed using the detected first heart rate, the detected second heart rate, an at rest heart rate of the user, and one or more factors selected from an age of the user, a gender of the user, a weight of the user, a height of the user, and a percent of the body weight attributed to muscle of the user.

According to an aspect of the invention, the controller calculates different rates of change for the heart rate during the exercise period based upon the detected first and second heart rates.

According to an aspect of the invention, the controller calculates: a first calorie consumption component having a first rate of change during a first time period substantially at a beginning of the exercise period and during which time the user's heart rate is changing from the detected first heart rate to the detected second heart rate, and a second calorie consumption component having a second rate of change at a second time period after the first time period and during which time the user's heart rate is substantially the detected second heart rate.

According to an aspect of the invention, the first time period is ten percent of the exercise period and the second time period is ninety percent of the exercise period.

According to an aspect of the invention the controller calculates a first calorie consumption rate using the detected first heart rate, and a second calorie consumption rate using the detected second heart rate, and the controller integrates a difference between the calculated first and second calorie consumption rates over a warm up time during which the heart rate is not constant in order to calculate calories consumed during the warm up time of the exercise period.

According to an aspect of the invention, the controller calculates a rate of change of the calorie consumption rate during the warm up time to be increasing at a substantially constant rate.

According to an aspect of the invention, the controller calculates the rate of change to be substantially a difference between the calculated first and second calorie consumption rates divided by the warm up time.

According to an aspect of the invention, the controller calculates a second calorie consumption rate using the detected second heart rate, the controller calculates a regular calorie consumption rate using an at rest heart rate, the at rest heart rate being a heart rate substantially at a time when the user first awakes from sleep, and the controller integrates a difference between the calculated second and regular calorie consumption rates over a steady portion of the exercise period during which the heart rate is constant and after a warm up time during which the heart rate is not constant.

According to an aspect of the invention, a rate of change of the calorie consumption rate during the steady portion is substantially zero.

According to an aspect of the invention, the controller further integrates a difference between a first calorie consumption rate and the second calorie consumption rate over the warm up time within the exercise period during which the heart rate is not constant, and the controller calculates the first calorie consumption rate using the detected first heart rate.

According to an aspect of the invention, the controller also integrates a difference between the first calorie consumption rate and the regular calorie consumption rate over the exercise period.

According to an aspect of the invention, the warm up time conforms to ten percent of the exercise period and the second point in the exercise period conforms to ninety percent of the exercise period.

According to an aspect of the invention, the regular component is $T*Y_0$, the warm up exercise component is $(T/10)*(Y_1(2)-Y_1(1))*0.5$, the exercise component is $(9T/10)*(Y_1(2)-Y_1(1))$, $Y_0=0.01808*(X(1)-A+20.25)+C$, $Y_1(1)=B_m*(X(1)-A)+C+0.3645$, $Y_1(2)=B_m*(X(2)-A)+C+0.3645$, $X(1)$ is the detected first heart rate, $X(2)$ is the detected second heart rate, A is the heart rate while the user is at rest, C is a constant relating to a coefficient of basal metabolic rate per minute, T is the exercise period, $B_m=0.0109*(LBM/H^2)-0.0023*(\%FAT)-0.0007*(age)-0.0211$, LBM is a percent of body mass attributed to muscle, H is height, and age is an age of the user.

According to an aspect of the invention, the regular component is $T*Y_0$, the warm up exercise component is $(T/10)*(Y_1(2)-Y_1(1))*0.5$, the exercise component is $(9T/10)*(Y_1(2)-Y_1(1))$, $Y_0=0.00895*(X(1)-A+20.25)+C$, $Y_1(1)=B_f*(X(1)-A)+C+0.1812$, $Y_1(2)=B_f*(X(2)-A)+C+0.1812$, $X(1)$ is the detected first heart rate, $X(2)$ is the detected second heart rate, A is the heart rate while the user is at rest, C is a constant relating to a coefficient of basal metabolic rate per minute, T is the exercise period, $B_f=0.0140(LBM/H^2)-0.0012(\% FAT)-0.1254$, LBM is a percent of body mass attributed to muscle, H is height, and age is an age of the user.

According to an aspect of the invention, the device may further include at least one processor including the controller which further reproduces audio and/or video data stored in a memory connected to the measuring device.

According to an aspect of the invention, the at least one processor decodes and outputs audio and/or video data encoded in a format selectable between data encoded according to an MPEG standard and a windows media standard.

According to an aspect of the invention, the device may further include a housing and a battery within the housing which provides power to the at least one processor, wherein the controller is disposed in the housing and the pulse input unit includes an indentation in the housing sized to receive a finger tip.

According to an aspect of the invention, the first point is at a beginning of the exercise period, and the second point is an end of the exercise period.

According to an aspect of the invention, the measuring device includes a hand held portable electrical device.

According to an aspect of the invention, at the first point, the controller notifies the user to take a pulse using the pulse input unit to obtain the first heart rate and, at the second point, the controller notifies the user to take another pulse using the pulse input unit to obtain the second heart rate, and for at least a potion of the exercise period other than at the first and second points, the user does not take a pulse using the pulse input unit.

According to an aspect of the invention, a method of measuring calorie consumption of a user includes detecting a first heart rate of the user at a first point in an exercise period and a second heart rate of the user at a second point of the exercise period other than the first point; and calculating calories consumed during the exercise period using the detected first heart rate, the detected second heart rate, an at rest heart rate of the user, and one or more factors selected between an age of the user, a gender of the user, a weight of the user, a height of the user, and a percent body mass attributed to muscle of the user.

According to an aspect of the invention, the calculating the calories consumed includes determining an exercise component corresponding to calories consumed during an exercise period, and the exercise component has a discontinuous rate of change for the heart rate between the first and second periods based upon the detected first and second heart rates.

According to an aspect of the invention, the determining the exercise component includes determining a first calorie consumption component during a first time period substantially at a beginning of the exercise period and during which time the user's heart rate is changing from the detected first heart rate to the detected second heart rate, and determining a second calorie consumption component at a second time period after the first time period and during which time the user's heart rate is substantially the detected second heart rate.

According to an aspect of the invention, the first time period is ten percent of the exercise period and the second time period is ninety percent of the exercise period.

According to an aspect of the invention, the calculating of the calories consumed includes calculating a first calorie consumption rate using the detected first heart rate, calculating a second calorie consumption rate using the detected second heart rate, and determining a warm up exercise component by integrating a difference between the first and second calorie consumption rates over a warm up time within the exercise period when the heart rate is not constant.

According to an aspect of the invention, the determining the warm up exercise component includes calculating a rate of change of the calorie consumption rate during the warm up time to be increasing at a substantially constant rate.

According to an aspect of the invention, the rate of change is a difference between the calculated first and second calorie consumption rates divided by the warm up time.

According to an aspect of the invention, the calculating the calories consumed includes calculating a second calorie consumption rate using the detected second heart rate, calculating a regular calorie consumption rate using an at rest heart rate measured when the user is substantially a time for first awakening, and determining an exercise component of the calories consumed by integrating a difference between the calculated second and regular calorie consumption rates over a steady portion of the exercise period during which the heart rate is constant and after a warm up time during which the heart rate is not constant.

According to an aspect of the invention, a rate of change of the calorie consumption rate during the steady portion after the warm up time is substantially zero.

According to an aspect of the invention, the calculating the calories consumed further includes calculating a first calorie consumption rate using the detected first heart rate, and determining a warm up exercise component by integrating a difference between the calculated first calorie consumption rate and the calculated second calorie consumption rate over the warm up time within the exercise period during which the heart rate is not constant.

According to an aspect of the invention, the calculating the calories consumed further includes calculating a regular component by integrating a difference between the calculated first and regular consumption rates over the exercise period.

According to an aspect of the invention, the warm up time conforms to ten percent of the exercise period and the second point in the exercise period conforms to ninety percent of the exercise period.

According to an aspect of the invention, the calculating the calories consumed further includes determining a gender of the user; if the user is one of a male and a female, the regular component is $T*Y_0$, the warm up exercise component is $(T/10)*(Y_1(2)-Y_1(1))*0.5$, the exercise component is $(9T/10)*(Y_1(2)-Y_1(1))$, $Y_0=0.01808*(X(1)-A+20.25)+C$, $Y_1(1)= B_m*(X(1)-A)+C+0.3645$, $Y_1(2)=B_m*(X(2)-A)+C+0.3645$, $X(1)$ is the detected first heart rate, $X(2)$ is the detected second heart rate, A is the heart rate while the user is at rest, C is a constant relating to a coefficient of basal metabolic rate per minute, T is the exercise period, $B_m=0.0109*(LBM/H^2)-0.0023*(\% FAT)-0.0007*(age)-0.0211$, LBM is a percent of body mass attributed to muscle, H is height, and age is an age of the user; and if the user is the other one of the male and the female, the regular component is $T*Y_0$, the warm up exercise component is $(T/10)*(Y_1(2)-Y_1(1))*0.5$, the exercise component is $(9T/10)*(Y_1(2)-Y_1(1))$, $Y_0=0.00895*(X(1)-A+20.25)+C$, $Y_1(1)=B_f*(X(1)-A)+C+0.1812$, $Y_1(2)=B_f*(X(2)-A)+C+0.1812$, $X(1)$ is the detected first heart rate, $X(2)$ is the detected second heart rate, A is the heart rate while the user is at rest, C is a constant relating to a coefficient of error per minute, T is the exercise period, $B_f=0.0140(LBM/H^2)-0.0012(\% FAT)-0.1254$, LBM is a percent of body mass attributed to muscle, H is height, and age is an age of the user.

According to an aspect of the invention, a computer readable medium is encoded with processing instructions to implement a method performed by a computer, the method including detecting a first heart rate of the user at a first point in an exercise period and a second heart rate of the user at a second point of the exercise period other than the first point; and calculating calories consumed during the exercise period using the detected first heart rate, the detected second heart rate, an at rest heart rate of the user, and one or more factors selected from an age of the user, a gender of the user, a weight of the user, a height of the user, and percent of body mass attributed to muscle, where the equation is usable without requiring a third heart rate detected during the exercise period.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE EMBODIMENTS

Reference will now be made in detail to the embodiments of the present invention, examples of which are illustrated in the accompanying drawings, wherein like reference numerals refer to the like elements throughout. The embodiments are described below in order to explain the present invention by referring to the figures.

Figure 1:
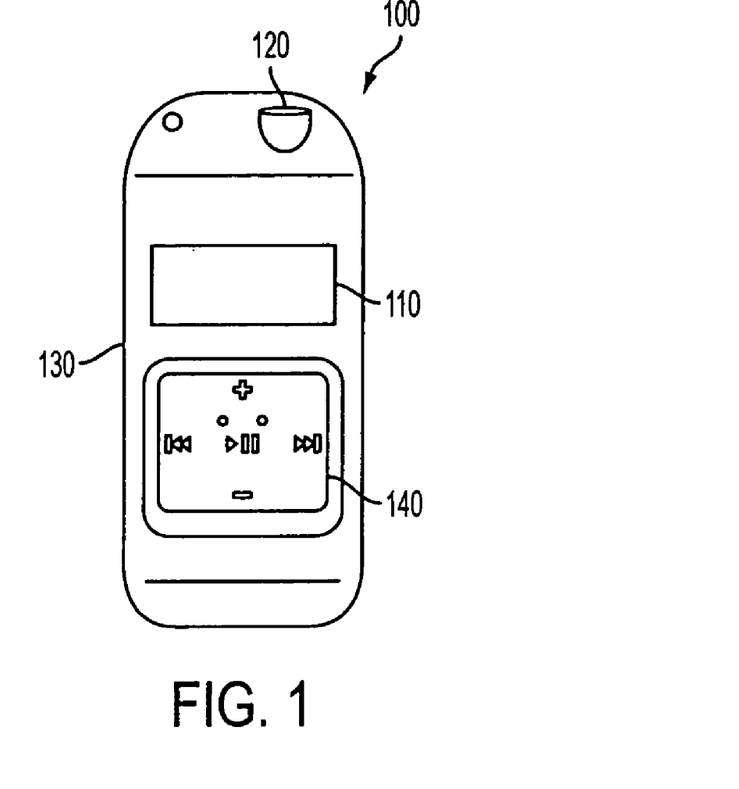
FIG. 1 shows a portable digital audio player having a calorie measuring device according to an embodiment of the invention.

According to an aspect of the invention shown in FIG. 1, a calorie measuring device 100 includes a body 110 having disposed thereon a pulse measuring device 120. As shown, the pulse measuring device 120 measures the pulse based upon a fingertip, which is depressed therein and from which the pulse (i.e., heart rate) is measured. Specifically, the pulse measuring device 120 uses an optical signal adopting photoplethysmography to develop a signal based upon a pulse detected from a finger placed on the pulse measuring device 120.

The shown pulse measuring device 120 is molded to the shape of a finger. However, it is understood that other mechanisms can be used to take a pulse, and that the pulse measuring device 120 need not be integrally connected to the body 110 in all aspects of the invention, and can instead be separately provided so as to connect to and transfer a detected pulse to the calorie measuring device 100.

The calorie measuring device 100 further includes a display 130, on which the measured number of calories are displayed. While not required in all aspects, the display 130 may further display other information processed by the calorie measuring device 100. Further shown are controls 140, which are used to indicate start and stop signals as well as other signals relevant to the operation of the calorie measuring device 100. However, it is understood that the display 100 need not be used in all aspects of the invention, and that the controls 140 need not be integral to the body 110 and instead may be separately provided so as to connect and transfer signals to the calorie measuring device 100. Further, it is understood that the controls 140 can be included in the display 110 where the display 110 includes a touch screen functionality.

As shown, the calorie measuring device 100 may further include a digital audio player, which allows the user to further listen to audio recorded in a digital audio format, such as audio data encoded in MP3, WMV, WMA, secure WMA, and other data formats. For example, the calorie measuring device 100 could be implemented in a modified SPORTS YEPP YP-60, produced by SAMSUNG ELECTRONICS CO., LTD. However, it is understood that other encoding formats can be used, that other types of digital audio players can be used, and that other types of portable digital data recorders can be used. By way of example, it is possible for the calorie device 100 to be included in a recorder having a display 130 suitable for reproducing video, as would be useful for portable DVD players or portable digital video recorders (DVRs) for use in displaying compressed video data. Further, it is understood that the calorie measuring device 100 could be implemented in a personal digital assistant (PDA), or a smart telephone, which includes functionalities from PDA's, and MP3 players and telephones in one unit. Further, it is understood that the calorie measuring device 100 could be implemented as a stand alone device used only for measuring the pulse and/or calories burned by an individual or a watch. It is understood that the present invention can be used in nonportable devices, such as exercise equipment, and need not be used in a portable device.

Figure 2:
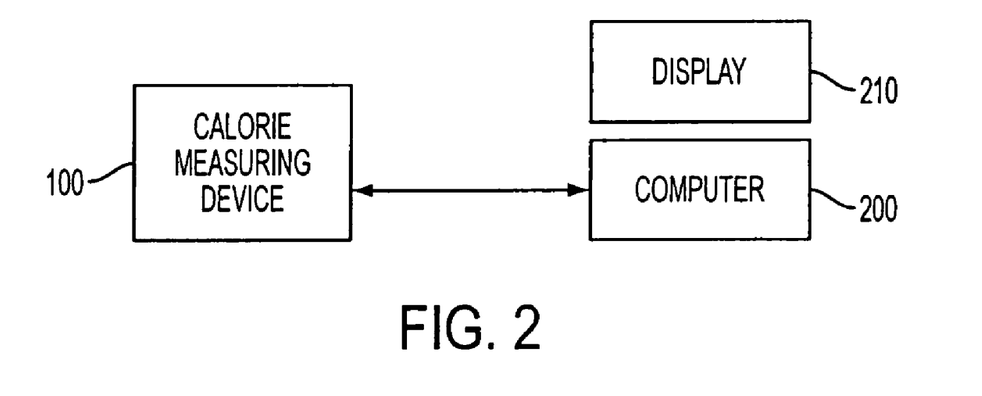
FIG. 2 is a block diagram showing an interaction between a computer and the calorie measuring device according to an embodiment of the invention.

According to an aspect of the invention shown in FIG. 2, the calorie measuring device 100 interfaces with a general or special purpose computer 200. The interface can be through a wired connection, such as through USB or IEEE 1396 connections and/or through a docking system which is connected to the computer 200, or through wireless systems such as Bluetooth, 802.11 wireless connections or other wireless standards. The computer 200 detects the measured heart rate stored in the calorie measuring device 100 and provides the results on a display 210.

Figure 3:
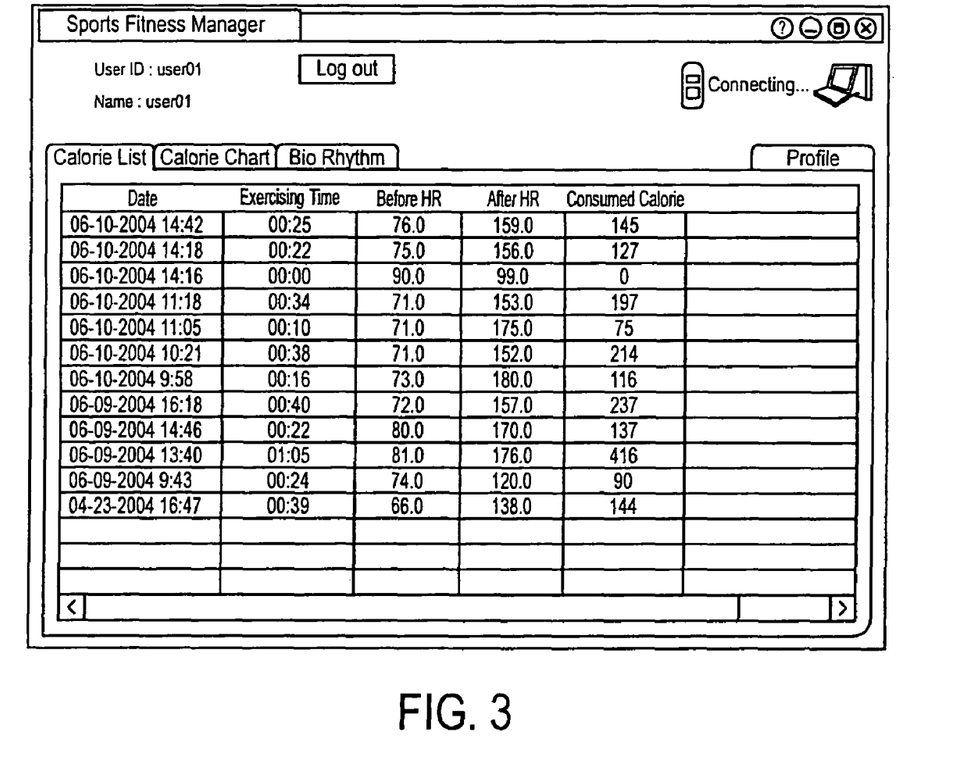
FIG. 3 shows a display reflecting past exercise periods and the calories consumed as measured using a calorie measuring method according to an embodiment of the invention.

An example of the displayed results is shown in FIG. 3, which shows a Sports Fitness Manager tracking dates, times of exercise, heart rates before and after exercise, and the consumed calories for each particular exercise session. The Sports Fitness Manager also charts the calories being consumed as a function of date, and will also provides a bio rhythm based upon the input birth date. The Sports Fitness Manager is implemented using software included on the computer 200 and imports the calorie consumption information. However, it is understood that the Sports Fitness Manager need not include each of the features shown in FIG. 3, and further need not be included in all aspects of the invention.

Figure 4:
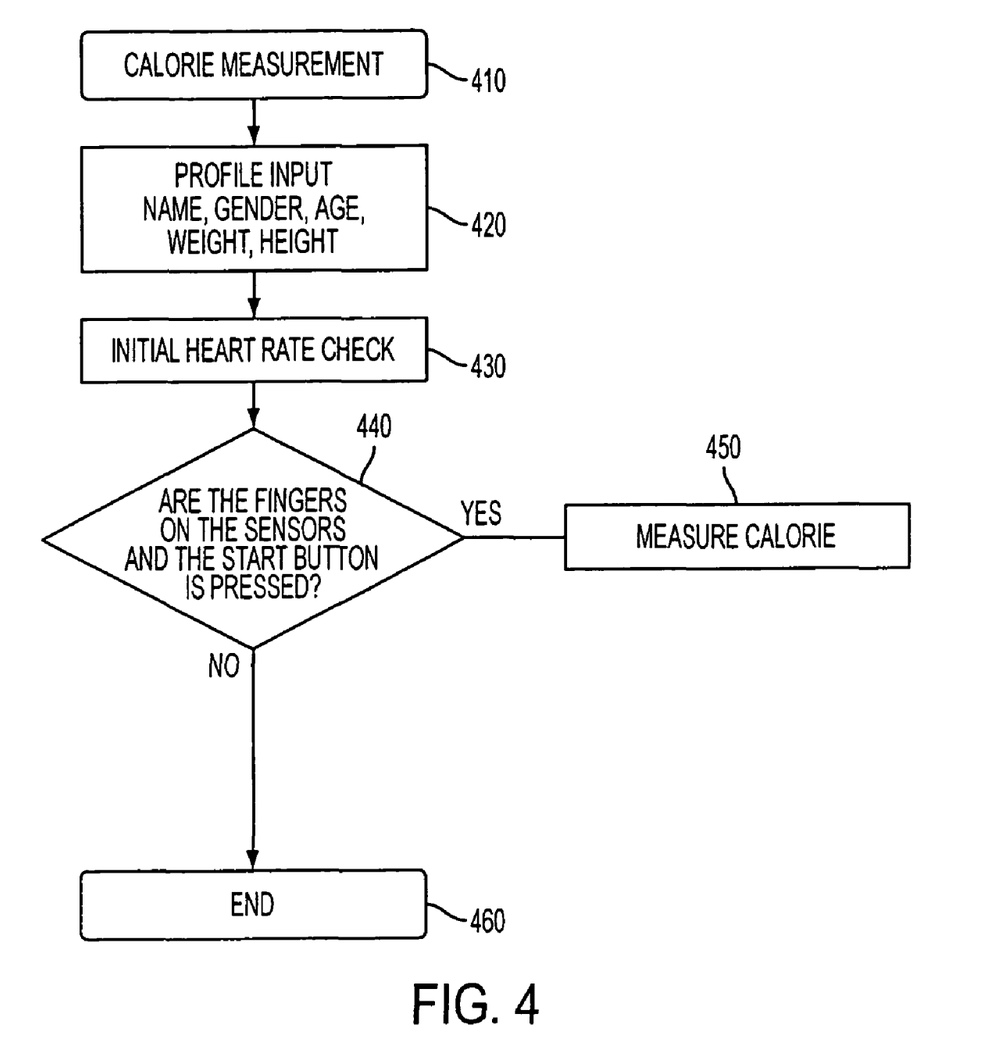
FIGS. 4 and 5 are flow charts of a method of measuring calories according to an embodiment of the invention.
Figure 5:
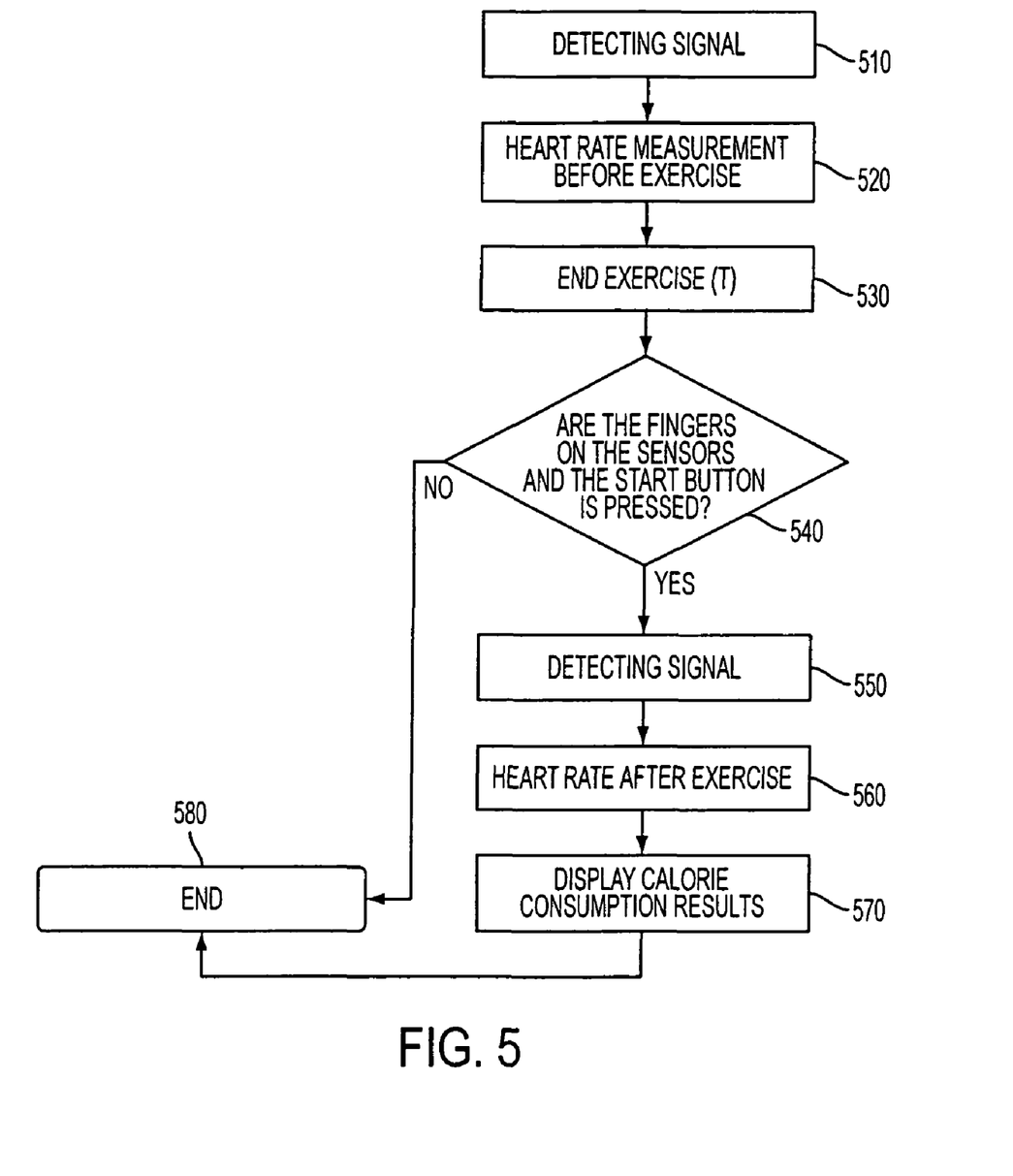

According to an aspect of the invention, the calorie measuring device 100 performs a method as shown in FIGS. 4 and 5. In FIG. 4, the user begins the calorie measuring process by indicating to the calorie measuring device 100 that the program is to begin (operation 410). In operation 420, the user inputs the name, the gender, the age, the weight, and the height of the user who desires to have their calorie measured.

Generally, the gender, age, height, and weight are used to calculate a body fat percentage. However, it is understood that the body fat percentage can also be input separately.

The gender, age, height, and weight are input in integer form. However, it is understood that the number can have other forms, and can be input with decimal places or using fractions. Further, this information can be input using the controls 140, or can be input by synchronizing with the Sports Fitness Manager or like program on the computer 200. It is further understood that not all elements need to be input, such as the name, in all aspects of the invention. However it is understood that use of a user name is helpful in order to distinguish cases where multiple people are using the same calorie measuring device 100.

In operation 430, the users initial heart rate is checked. Specifically, the user puts a finger on the pulse measuring device 120, in order to detect an at rest/regular heart rate. The regular heart rates determined in operation 430, as well as the factors entered in operation 420, are used to calculate calories burned during exercise. The regular heart rate of the individual is measured when the individual wakes up and before the individual gets out of bed. The regular heart rate is the regular heart rate is depicted graphically as element I in FIG. 6.

While not required in all aspects of the invention, the regular heart rate is measured in advance of the exercise period and is stored in the calorie measuring device 100. Further, while not required in all aspects of the invention, the input gender, age, weight, and height, and the regular heart rate is stored in a memory of the calorie measuring device 100 for later use. In this way, the individual need not repeat the detection of the regular heart rate in operation 430 and/or enter the gender, age, weight, and height each time the individual uses the calorie measuring device 100. It is understood that, instead of storing this data in an internal memory, one or more of the regular heart rate, gender, age, weight, height and/or name factors can be stored on and retrieved from an external memory, such as a memory stick, which is inserted into the calorie measuring device 100.

When the user wishes to measure calories consumed during an exercise period, the user needs to place a finger on the pulse measuring device 120 and presses a start button on the controls 140 in order to detect a pulse rate at the beginning of an exercise period. As such, in operation 440, the calorie measuring device 100 determines whether the fingers are on the pulse measuring device 120, and whether a start button of the controls 140 is pressed. The operation 440 detects whether the user is about to enter an exercise period for which the calories are to be measured.

If the start button has been pressed and the fingers are on the pulse measuring device 120 (i.e., also referred to generically as sensors), the calorie measuring device 100 measures the calories in operation 450. If the fingers are not on the sensors and the start button has not been pressed, the calorie measurement routine ends. While shown as requiring that the fingers be on the sensors and a start button be pressed in operation 440, it is understood that in aspects of the invention, the calorie measuring device 100 does not need a start button to be pressed, and instead can merely rely on whether the fingers have been detected on the sensors.

Operation 450 will be explained in further detail with regard to FIG. 5 according to an aspect of the invention. In FIG. 5, the calorie measuring device 100 begins detecting the pulse signal from the pulse measuring device 120 so as to detect the pulse before the exercise is begun.

Figure 6:
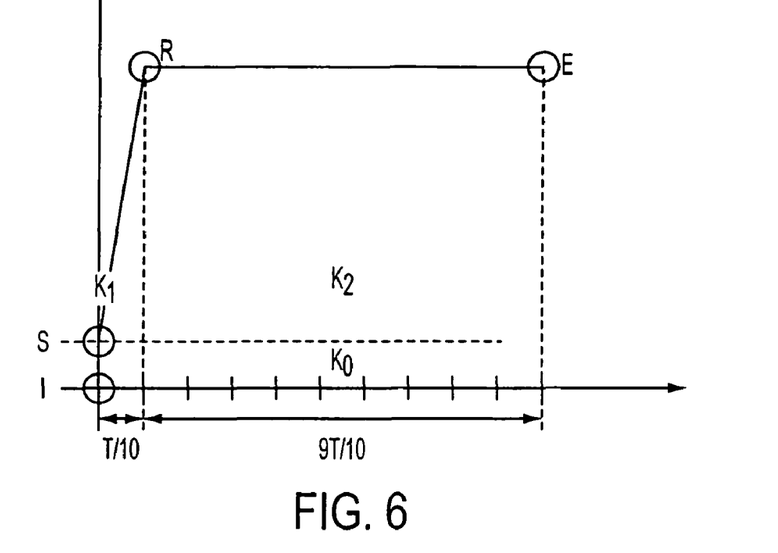
FIG. 6 is a graph showing the integration performed in the method of measuring calories according to an aspect of the invention.

By way of comparison, the heart rate measured before exercise 520 is shown by the letters shown in FIG. 6, whereas the regular heart rate measured in operation 430 is measured as shown in FIG. 6 as element I.

In operation 530, the user begins exercising and starts the exercise period T. After the exercise period T, the individual again measures the heart rate in operation 540 by putting a finger on the pulse measuring device 120 and pressing the start button. It is understood that the single start button need not be used to implement aspects of the invention, multiple buttons can be used in order to prevent confusion, or a switch can be used to toggle between positions.

If the fingers are on the pulse measuring device 120, and the start button has been pressed in operation 540, the heart rate is detected in operation 550. The heart rate after exercise is measured based on the detected signal in operation 560. As shown in FIG. 6, the heart rate after exercise is shown as element E.

After operation 560, the calorie measuring device 100 calculates the calories consumed as explained below in greater detail, and the results are displayed on the display 110 in operation 570. After the display in 570, the calorie measuring operation is concluded in operation 580. While not required in all aspects, it is understood that the heart rate and the calorie consumed can be stored and/or transferred to the computer 200 in order to create a log of heart rates, and measured calories consumed as shown in FIG. 3. Further, it is understood that operation 570 need not display the calorie results on the display 110 of the calorie measuring device 100, and instead can rely upon the display 210 of the computer 200. Such an embodiment of the invention might be useful where no display 130 is included on the calorie measuring device 100.

If the fingers are not on the sensors and/or the start button is not pressed in operation 540, the operation ends in operation 580. In this way, if the individual loses interest in measuring the calories consumed, the routine is ended. The calorie measuring device 100 can determine whether the calorie measuring routine is be ended if the start button is not pressed within a predetermined time after the exercise is believed to have begun, and if the individual indicates through the controls 140 that the routine is to be terminated. Additionally, if the expected exercise period T is entered by the user at the beginning of the exercise period, if the exercise start button is not pressed within a predetermined period after the expected exercise period T is concluded, the calorie measuring device 100 can conclude the calorie measuring routine in operation 580. However, it is understood that other mechanisms for terminating the routine can be implemented, and that the termination of the routine need not be performed at operation 540 in all aspects of the invention.

According to an aspect of the invention, the calorie measuring device 100 indirectly measures the calorie consumption in operation 570 using the heart rate monitored before and after exercise without requiring measurement of the heart rate during the exercise. As such, while it is possible to utilize additional heart rates measured during exercise, such additional data points are not required.

Specifically, an embodiment of the calorie measuring device 100 uses an indirect calorie measurement technique in which the amount of oxygen consumption is measured based upon the heart rate. Since the amount of oxygen consumed relates to the energy consumed in a time period, it possible to know the amount of calories consumed according to the oxygen consumed. According to an aspect of the invention, the calorie measuring device 100 uses a relationship between the oxygen consumed, user's gender, age, height, weight, and the user's heart rate before and after exercise.

According to an aspect of the invention, the formulas for the calorie consumption rate are provided in Equations 1 and 2. Equation 1 is for calorie consumption rate during rest for both male and females.

Male: $Y_0(\text{kcal/min})=0.01808(X-A+20.25)+C$

Female: $Y_0(\text{kcal/min})=0.00895(X-A+20.25)+C$  Equation 1

In Equation 1, the 0.01808 coefficient for Males, and the 0.00895 coefficient for females represents an average of X. These averages are obtained from formulas for calorie consumption during the regular heart rate. Further, A is the regular heart rate measured during operation 430, and X is the heart rate during measurement in operation 520 (i.e., at the beginning of the exercise period T). C is a coefficient of basal metabolic rate per minute. The measurement is in kcal/min, $C=c*a/60$, where c is the Coefficient of regular heart rate per skin area (kcal/m$^2$/h) and a is a surface area of skin (cm$^2$) $=W0.444*H0.663*88.83$ (for people of 6 years or older). W is the weight (e.g., in kg) and H is the height (e.g., in cm). Calorie consumption is calculated based from the subject's height and the value of a. Further, the value of 20.25 within the Equation 1 formula is the average difference between the regular heart rate in a lying down position and the regular heart rate in an upright position.

Graphically, Equation 1 is shown as area K0 is FIG. 6. Thus, at the beginning of the exercise period T using the heart rate taken in operations 430 and 520, the area K0 is Y1*T.

Generally, c is a basal metabolic rate in the body as set forth below in Table 1 and further discussed in Japanese patent publication no. 08-52119, based upon Public Welfare Annuity Hospital Annual Report, volume 17, p201-206 (1990), and/or with Company Height Medical Science, Hirosaki Medical Department Report, volume 40-1, p60-69 (1988).

TABLE 1

| Basal Metabolic Rate (kcal/rrf/h) | | |
|---|---|---|
| Age | Men | Women |
| 0 | 48.7 | 48.4 |
| 1 | 53.6 | 52.6 |
| 2 | 56.2 | 56.1 |
| 3 | 57.2 | 55.6 |
| 4 | 56.3 | 54.0 |
| 5 | 55.1 | 51.6 |
| 6 | 52.9 | 49.5 |
| 7 | 51.1 | 47.6 |
| 8 | 49.3 | 46.2 |
| 9 | 47.5 | 44.8 |
| 10 | 46.2 | 44.1 |
| 11 | 45.3 | 43.1 |
| 12 | 44.5 | 42.2 |
| 13 | 43.5 | 41.2 |
| 14 | 42.8 | 39.8 |
| 15 | 41.7 | 38.1 |
| 16 | 41.0 | 36.9 |
| 17 | 40.3 | 36.0 |
| 18 | 39.6 | 35.6 |
| 19 | 38.8 | 35.1 |
| 20-29 | 37.5 | 34.3 |
| 30-39 | 36.5 | 33.2 |
| 40-49 | 35.6 | 32.5 |
| 50-59 | 34.8 | 32.0 |
| 60-64 | 34.0 | 31.8 |
| 65-69 | 33.3 | 31.4 |
| 70-74 | 32.6 | 31.1 |
| 75-79 | 31.9 | 30.9 |
| 80- | 30.7 | 30.0 |

Equation 2 is the Formula for calorie consumption rate during exercise for males and females.

Male: $Y_1=B_m(X-A)+C+0.3645$

Female: $Y_1=B_f(X-A)+C+0.1812$  Equation 2

In Equation 2, $B_m=0.0109(\text{LBM}/H^2)-0.0023(\%\text{ FAT})-0.0007(\text{age})-0.0211$. $B_f=0.0140(\text{LBM}/H^2)-0.0012(\%\text{ FAT})-0.1254$. X is the heart rate during the exercise period T (i.e., measured in operations 560 and 520), and A is the at rest heart rate before the exercise period T (i.e., measured in operation 430).

LBM is the percent of body mass attributed to muscle and is therefore equal to $W(1-\%\text{ FAT})$. % FAT is the percent body fat of the individual.

In Equation 2, when looking at the calorie consumption rate during exercise, it is observed that, as compared to the rate during rest, the differences between individual people are apparent. Specifically, it was found that the coefficient of X for men, Bm, is proportional to the weight minus the weight of fat in the body (weight−% FAT*weight) divided by the square of the height. Thus, the coefficient of X for men Bm was inversely proportional with age and percent body fat.

For women, the coefficient of X for men Bf was found to be proportional to $(\text{LBM}/\text{Ht}^2)$ and inversely proportional to percent body fat. However, there was no clear relation with age such that Equation 2 does not include an age factor for women.

While it is possible to directly input body fat values to input the % FAT factor used in equations 1 and 2, the calorie measuring device 100 calculates the % FAT according to the height H, weight W, age A, and gender as follows in Equations 3 through 8. Specifically, Equation 3 is for males of Ages 10~16, Equation 4 is for females of Ages 10~16, Equation 5 is for males of Ages 17~18, Equation 6 is for females of Ages 17~18, Equation 7 is for males of Ages 19 and beyond, and Equation 8 is for females of Ages 19 and beyond.

$$f = 0.0005870H^2 - 2.761 \times 10^6 \frac{1}{(R-23.091)^2} +$$
$$0.0002813 \times 10^6 \frac{H^2}{(R-23.091)^2} +$$
$$0.0094R + 0.443W - 12.75 \quad \text{Equation 3}$$

$$f = 0.0004907H^2 - 2.27 \times 10^6 \frac{1}{(R-23.091)^2} +$$
$$0.0002275 \times 10^6 \frac{H^2}{(R-23.091)^2} + 0.349W + 2.830 \quad \text{Equation 4}$$

$$f = 0.0005802H^2 - 2.682 \times 10^6 \frac{1}{(R-23.091)^2} +$$
$$0.000277 \times 10^6 \frac{H^2}{(R-23.091)^2} +$$
$$0.006975R + 0.371W - 6.05806 \quad \text{Equation 5}$$

$$f = 0.0004867H^2 - 2.261 \times 10^6 \frac{1}{(R-23.091)^2} +$$
$$0.0002266 \times 10^6 \frac{H^2}{(R-23.091)^2} - 0.0026R + 0.299W + 81 \quad \text{Equation 6}$$

$$f = 0.0005742H^2 - 2.666 \times 10^6 \frac{1}{(R-23.091)^2} +$$
$$0.0002688 \times 10^6 \frac{H^2}{(R-23.091)^2} +$$
$$0.00369R + 0.3W - 0.09A + 3.149794 \quad \text{Equation 7}$$

-continued $$f = 0.0004871H^2 - 2.286 \times 10^6 \frac{1}{(R-23.091)^2} + \\ 0.0002250 \times 10^6 \frac{H^2}{(R-23.091)^2} - \\ 0.0054R + 0.25W - 0.068A + 14.7057$$

Equation 8

In Equations 3 through 8, f=weight−minus weight of fat (i.e., LBM in Equation 2). % FAT=((weight f)/weight)×100, and R is the electrical resistance of body. In a male, R is 635, and in a female, R is 833. H is height (cm), W is weight (kg), and A is age.

Using Equations 1 and 8, the calories consumption is obtained directly from the heart rate according to an aspect of the invention. However, it is understood that, if the percent body fat is independently derived and input, only Equations 1 and 2 are used according to an aspect of the invention.

As shown graphically in FIG. 6, the oxygen consumed prior to exercise is related to an area K0, which extends from the regular heart rate at element I and the heart rate at the beginning of exercise at element S and extends for the entire exercise period T. The area K0 is the calorie consumption during rest and relates to the calories consumed in the individual's normal routine. The heart rate at element I corresponds to the regular heart rate, which is generally input ahead of time in operation 430 and is measured up to a minute from when the subject wakes up from sleep in bed, right before the subject gets up. In contrast, the heart rate at element S is measured in operation 520 at the beginning of the exercise period T.

The oxygen consumed during exercise is related to areas K1 and K2, which extend from the heart rate at element S at the beginning of the exercise, to the heart rate at element E at the end of the exercise period T. However, since the heart rate is generally only constant after a warm up period at approximately 1/10 of the exercise period T (i.e., at element R), the oxygen consumed during the warm up period is related to the area K1.

As shown graphically in FIG. 6, the area K1 is depicted as a triangular region extending from the heart rate at element S to the heart rate at element R over a period T/10. The area K1 is the calorie consumption rate after starting exercise up to peak heart rate (10% of total exercise period T). While it might be possible to have the user enter a heart rate substantially at element R at the period T/10 according to an aspect of the invention, the calorie measuring device 100 assumes that the heart rate at element R is the same as the heart rate at the end of the exercise period T at element E. As such, this additional data point is not required.

The area K2 is depicted as a rectangular region extending from the heart rate at element R to the heart rate at element E over a period 9T/10. The area K2 is the calorie consumption rate during a maximum sustained heart rate (90% of the exercise period T). While not required, it is understood that, since the heart rate is constant during this period, instead of measuring the heart rate at element E, the second heart rate could be measured between elements R and element E so long as the end of the exercise period T is measured or input. However, in order to reduce the number of operations a user must perform, the second heart rate according to an aspect of the invention is measured at element E so as to simultaneously record the end of the exercise period T.

In order to determine the calories consumed, the relationship between time and the heart rate is integrated. Using the simplified model shown in FIG. 6, the calorie consumption is measured as the sum of the areas K0+K1+K2. Thus, using Equation 1, the heart rate at the beginning of exercise X(S) is measured at element S and the heart rate at rest (A) is measured at element I so as to obtain the calorie consumption rate prior to exercise: Y0. K0=Y0*T.

Using Equation 2, the calorie consumption rate at element S (Y1(S)) is calculated using the heart rate detected in operation 520 at the beginning of the exercise period T in order to obtain element S, and the calorie consumption rate at element E (Y1(E)) is detected in operation 560 at the end of the exercise period T. Thus, K1=((Y1(E)−Y(Y1(S))*0.1*T)*0.5, and K2=((Y1(E)−Y(Y1(S))*0.9*T.

In FIG. 6, element I is at t=0, hr__0, element S is at t=0, hr__1, element R is at T/10, hr__2, and element E is at t=T, hr__2. Further, hr__0 is the heart rate at rest, hr__1 is the heart rate before exercise, and hr__2 is the heart rate after exercise. T is the total exercise period. From the above, the Total Calorie Consumption can be calculated as K0+K1+K2.

Figure 7:
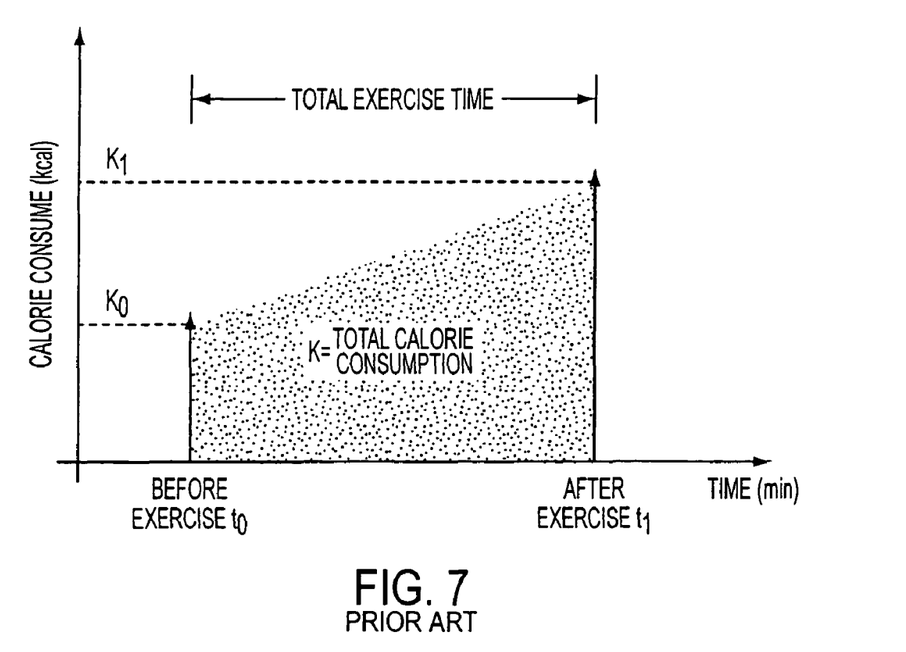
FIG. 7 is a graph showing an integration performed in another method of measuring calories.

Experimentally, the number of calories consumed calculated by the calorie measuring device 100, implemented using a modified sports YEPP YP-60 made by SAMSUNG ELECTRONICS CO., LTD, modified according to an aspect of the invention, were compared against the number of calories consumed as measured using three reference devices: the POLAR A3, made by POLAR of Finland, a treadmill, and the unmodified YEPP YP-60 released February 2004 using an old method shown graphically in FIG. 7 (referred to in Tables 2 and 3 as the "Old Method"). The subjects in these tests were 10 adult males and females in their 20s and 30s in a physical training area.

In regards to the Old Method used to calculate calories consumed, the calories consumed are measured based upon Equation 9:

$K(\text{Total Calorie Consumption}) = t_1 k_0 + 0.5 t_1 (k_1 - k_0)$. Equation 9:

In Equation 3, t1 is the time at the conclusion of the exercise period, k1 is the calories consumed at the end of the exercise period, $t_0$ is the time at the beginning of the exercise period, and k0 is the calories consumed at the beginning of the exercise period. As can be seen in Equation 3 and graphically in FIG. 7, the Old Method assumes a constant slope of the consumed calories as a function of time from a beginning of the exercise period to an end of the exercise period and therefore does not account for a change in the slope occurring at element R shown in FIG. 6. In contrast, the calorie measuring device 100 according to an aspect of the invention accounts for the change in slope occurring after a warm up period.

In addition, the method performed by the POLAR A3 device involves continuous heart monitoring during exercise. As such, while the calorie measuring device 100 shown in FIG. 1 uses an optical signal adopting photoplethysmography to develop a signal based upon a pulse detected from a finger placed on the pulse measuring device 120, the POLAR A3 device uses an electrocardiogram to generate an electrical signal based upon a sensor placed on the chest of the user. While, the POLAR A3 device conducts continuous heart rate monitoring during exercise, the POLAR 43 device is more invasive in requiring a transmitter to be attached to the user's chest during the exercise period and is also expensive. In contrast, the calorie measuring device 100 is able to simply measure the calories consumed in a non-intrusive way by measuring heart rates before and after exercise while also maintaining a low price.

Further, the conventional treadmill measures the number of calories consumed based upon the speed of the treadmill and the time on the treadmill as opposed to using the heart rate.

The results of the experiment are provided in Tables 2 and 3.

TABLE 2

Comparison of Total Calorie Consumption During Exercise

|  | Exercise Type | Old method (Kcal) | New method (Kcal) | Polar (Kcal) | Treadmill (Kcal) |
|---|---|---|---|---|---|
| subject 01 | Running | 88 | 115 | 132 | 94 |
| subject 02 | Running | 151 | 363 | 300 | 204 |
| subject 03 | Running | 268 | 356 | 413 | 396 |
| subject 04 | Running | 159 | 291 | 292 | 239 |
| subject 05 | Running | 142 | 245 | 254 | 261 |
| subject 06 | Power Walking | 187 | 268 | 342 | 237 |
| subject 07 | Power Walking | 111 | 151 | 163 | 158 |
| subject 08 | Power Walking | 152 | 180 | 221 | 208 |
| subject 09 | Running + Power Walking | 173 | 270 | 289 | 287 |
| subject 10 | Running + Power Walking | 146 | 262 | 279 | 242 |

TABLE 3

Residual analysis of Total Calorie Consumption During Exercise (Residual = Reference device − Test device)

|  | Exercise Type | Polar vs. Old Method (kcal) | Polar vs. New Method (kcal) | Treadmill vs. Old Method (kcal) | Treadmill vs. New Method (kcal) | Treadmill vs. Polar (kcal) |
|---|---|---|---|---|---|---|
| subject 01 | Running | 44 | 17 | 6 | −21 | −38 |
| subject 02 | Running | 149 | −63 | 53 | −159 | −96 |
| subject 03 | Running | 145 | 57 | 128 | 40 | −17 |
| subject 04 | Running | 133 | 1 | 80 | −52 | −53 |
| subject 05 | Running | 112 | 9 | 119 | 16 | 7 |
| subject 07 | Power Walking | 155 | 74 | 50 | −31 | −105 |
| subject 07 | Power Walking | 52 | 12 | 47 | 7 | −5 |
| subject 08 | Power Walking | 69 | 41 | 56 | 28 | −13 |
| subject 09 | Running + Power Walking | 116 | 19 | 114 | 17 | −2 |
| subject 10 | Running + Power Walking | 133 | 17 | 96 | −20 | −37 |
| Average |  | 110.8 | 18.4 | 74.9 | −17.5 | −35.9 |
| Standard Deviation |  | 41.2 | 36.7 | 39.1 | 57.4 | 38.7 |

Based upon the above results, the relative accuracy of the total calorie consumption for the calorie measuring device 100 implemented in the modified YEPP YP-60 according to an aspect of the invention (i.e., the test device) were made while exercise was being performed. The results are provided in Table 4. In Table 4, the Measurement Percent Error (%)= (|Cr−Ct|/Cr)*100, where Cr is the calorie consumption rate from a reference measurement device, and Ct is the calorie consumption rate from the calorie measuring device 100 (i.e., the testing device).

TABLE 4

Comparison of Accuracy Total Calorie Consumption During Exercise

| Reference Device | Testing Device Percent Error (%) |
|---|---|
| POLAR A3 | 11.18 |
| Treadmill | 18.34 |

By way comparison, the treadmill Percent Error with reference to the POLAR A3 device was 18.63%, and the POLAR A3 percent Error with reference to the Treadmill was 13.94%. As a result of comparing between the calorie measurements from the POLAR device and measurements from the treadmill, it was observed that the error percentage with respect to the calorie measuring device 100 on both the POLAR A3 and the treadmill is less than the error percentage between the POLAR A3 and the treadmill. As such, the calorie measuring device 100 of the present invention provides comparable results to the POLAR A3 and the treadmill at a greatly reduced cost using a portable device having a non-invasive sensor.

While not required, it is understood that the method of the present invention can be implemented using computer software/processing instructions stored on a computer readable medium. Such software can be distributed on a computer readable medium, implemented as firmware, and/or downloaded to upgrade an existing apparatus to include the calorie measuring method of the present invention.

According to an aspect of the invention, it is possible to simply measure the calorie consumption by measuring the heart rate before and after exercising. According to an aspect of the invention, by using the heart rate measured before exercising, it can instruct the user the most appropriate exercise intensity and time by measuring the calorie consumption during exercise. According to an aspect of the invention, it is possible to apply the calorie consumption measuring device on other portable platforms, as well as other non-portable platforms.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A measuring device for use in measuring calories consumed by a user, comprising:
    a pulse input unit which detects a first heart rate of the user at a first point in an exercise period and a second heart rate of the user at a second point of the exercise period other than the first point, the pulse input unit not detecting a third heart rate between the first and second points; and
    a controller which receives the detected first and second heart rates and calculates calories consumed using the detected first heart rate, the detected second heart rate, an at rest heart rate of the user, and one or more factors selected from an age of the user, a gender of the user, a weight of the user, a height of the user, and a percent of the body weight attributed to muscle of the user, wherein the controller calculates different calorie consumption rates during the exercise period based upon the detected first and second heart rates.

2. The measuring device of claim 1, wherein the controller calculates:

a first calorie consumption component having a first rate of change during a first time period substantially at a beginning of the exercise period and during which time the user's heart rate is changing from the detected first heart rate to the detected second heart rate, and a second calorie consumption component having a second rate of change at a second time period after the first time period and during which time the user's heart rate is substantially the detected second heart rate.

3. The measuring device of claim 2, wherein the first time period is ten percent of the exercise period and the second time period is ninety percent of the exercise period.

4. The measuring device of claim 1, wherein the first point is at a beginning of the exercise period, and the second point is an end of the exercise period.

5. The measuring device of claim 4, wherein the measuring device comprises a hand held portable electrical device.

6. A measuring device for use in measuring calories consumed by a user, comprising:

a pulse input unit which detects a first heart rate of the user at a first point in an exercise period and a second heart rate of the user at a second point of the exercise period other than the first point, the pulse input unit not detecting a third heart rate between the first and second points; and a controller which receives the detected first and second heart rates and calculates calories consumed using the detected first heart rate, the detected second heart rate, an at rest heart rate of the user, and one or more factors selected from an age of the user, a gender of the user, a weight of the user, a height of the user, and a percent of the body weight attributed to muscle of the user, wherein:

the controller calculates a first calorie consumption rate using the detected first heart rate, and a second calorie consumption rate using the detected second heart rate, and the controller integrates a difference between the calculated first and second calorie consumption rates over a warm up time during which the heart rate is not constant in order to calculate calories consumed during the warm up time of the exercise period.

7. The measuring device of claim 6, wherein the controller calculates a rate of change of the calorie consumption rate during the warm up time to be increasing at a substantially constant rate.

8. The measuring device of claim 7, wherein the controller calculates the rate of change to be substantially a difference between the calculated first and second calorie consumption rates divided by the warm up time.

9. A measuring device for use in measuring calories consumed by a user, comprising:

a pulse input unit which detects a first heart rate of the user at a first point in an exercise period and a second heart rate of the user at a second point of the exercise period other than the first point, the pulse input unit not detecting a third heart rate between the first and second points; and a controller which receives the detected first and second heart rates and calculates calories consumed using the detected first heart rate, the detected second heart rate, an at rest heart rate of the user, and one or more factors selected from an age of the user, a gender of the user, a weight of the user, a height of the user, and a percent of the body weight attributed to muscle of the user, wherein:

the controller calculates a second calorie consumption rate using the detected second heart rate, the controller calculates a regular calorie consumption rate using an at rest heart rate, the at rest heart rate being a heart rate substantially at a time when the user first awakes from sleep, and the controller integrates a difference between the calculated second and regular calorie consumption rates over a steady portion of the exercise period during which the heart rate is constant and after a warm up time during which the heart rate is not constant.

10. The measuring device of claim 9, wherein a rate of change of the calorie consumption rate during the steady portion is substantially zero.

11. The measuring device of claim 10, wherein the controller further integrates a difference between a first calorie consumption rate and the second calorie consumption rate over the warm up time within the exercise period during which the heart rate is not constant, and the controller calculates the first calorie consumption rate using the detected first heart rate.

12. The measuring device of claim 11, wherein:

the controller also integrates a difference between the first calorie consumption rate and the regular calorie consumption rate over the exercise period.

13. The measuring device of claim 12, wherein the warm up time conforms to ten percent of the exercise period and the second point in the exercise period conforms to ninety percent of the exercise period.

14. The measuring device of claim 13, wherein:

a regular component is $T * Y_0$, a warm up exercise component is $(T/10)*(Y_1(2)-Y_1(1))*0.5$, an exercise component is $(9T/10)*(Y_1(2)-Y_1(1))$, $Y_0=0.01808*(X(1)-A+20.25)+C$, $Y_1(1)=B_m*(X(1)-A)+C+0.3645$, $Y_1(2)=B_m*(X(2)-A)+C+0.3645$, $X(1)$ is the detected first heart rate, $X(2)$ is the detected second heart rate, A is the heart rate while the user is at rest, C is a constant relating to a coefficient of basal metabolic rate per minute, T is the exercise period, $B_m=0.0109*(LBM/H^2)-0.0023*(\% FAT)-0.0007*(age)-0.0211$, LBM is the percent of body mass attributed to muscle, H is the height, and age is the age of the user.

15. The measuring device of claim 13, wherein:

a regular component is $T * Y_0$, a warm up exercise component is $(T/10)*(Y_1(2)-Y_1(1))*0.5$, an exercise component is $(9T/10)*(Y_1(2)-Y_1(1))$, $Y_0=0.00895*(X(1)-A+20.25)+C$, $Y_1(1)=B_m*(X(1)-A)+C+0.1812$, $Y_1(2)=B_m*(X(2)-A)+C+0.1812$, $X(1)$ is the detected first heart rate, $X(2)$ is the detected second heart rate, A is the heart rate while the user is at rest, C is a constant relating to a coefficient of basal metabolic rate per minute,
T is the exercise period,
$B_f = 0.0140(LBM/H^2) - 0.0012(\% FAT) - 0.1254$,
LBM is the percent of body mass attributed to muscle,
H is the height, and
age is the age of the user.

16. The measuring device of claim 13, further comprising at least one processor including the controller which further reproduces audio and/or video data stored in a memory connected to the measuring device.

17. The measuring device of claim 16, wherein the at least one processor decodes and outputs audio and/or video data encoded in a format selectable between data encoded according to an MPEG standard and a windows media standard.

18. The measuring device of claim 13, further comprising a housing and a battery within the housing which provides power to the at least one processor, wherein the controller is disposed in the housing and the pulse input unit comprises an indentation in the housing sized to receive a finger tip.

* * * * *

UNITED STATES PATENT AND TRADEMARK OFFICE
CERTIFICATE OF CORRECTION

| | | |
|---|---|---|
| PATENT NO. | : 7,762,952 B2 | Page 1 of 1 |
| APPLICATION NO. | : 11/095551 | |
| DATED | : July 27, 2010 | |
| INVENTOR(S) | : Mi-Hee Lee et al. | |

It is certified that error appears in the above-identified patent and that said Letters Patent is hereby corrected as shown below:

Column 16, Line 63 delete "$B_m*$" and insert --$B_f*$--, therefore.

Column 16, Line 64 delete "$B_m*$" and insert --$B_f*$--, therefore.

Signed and Sealed this
Fourth Day of January, 2011

David J. Kappos
*Director of the United States Patent and Trademark Office*